United States Patent

Hijlkema et al.

[11] Patent Number: 5,846,199
[45] Date of Patent: Dec. 8, 1998

[54] CATHETER WITH MARKER SLEEVE

[75] Inventors: Lucas J. Hijlkema, Beetsterzwaag; Jan Thalens, Assen, both of Netherlands

[73] Assignee: Cordis Europa N.V., Netherlands

[21] Appl. No.: 842,588

[22] Filed: Apr. 15, 1997

[51] Int. Cl.⁶ .................................................. A61B 5/00
[52] U.S. Cl. ............................................................ 600/435
[58] Field of Search .................................. 600/433–435, 600/461, 462, 585

[56] References Cited

U.S. PATENT DOCUMENTS

| | | | |
|---|---|---|---|
| 3,605,750 | 9/1971 | Sheridan et al. | 128/348 |
| 3,618,614 | 11/1971 | Flynn et al. | 128/348 |
| 4,793,359 | 12/1988 | Shanow | 600/435 |
| 4,938,220 | 7/1990 | Mueller | 600/435 |
| 5,048,530 | 9/1991 | Herwitz | 600/461 |
| 5,253,653 | 10/1993 | Daigle et al. | 600/434 |
| 5,499,973 | 3/1996 | Saab | 600/435 |

FOREIGN PATENT DOCUMENTS

| | | | |
|---|---|---|---|
| 0 033 659 | 8/1981 | European Pat. Off. | A61M 25/00 |
| 0 255 369 | 8/1986 | European Pat. Off. | A61M 25/00 |
| 0 553 960 | 8/1993 | European Pat. Off. | A61F 2/06 |
| 38 33 365 | 4/1989 | Germany | A61B 6/00 |

*Primary Examiner*—Max Hindenburg
*Attorney, Agent, or Firm*—Paul A. Coletti

[57] ABSTRACT

The invention relates to a catheter comprising a tube-like basic body with a proximal and a distal end, marking means made of a material opaque to X-radiation arranged close to the distal end. The marking means may be formed by at least one tube-like marker sleeve made of a plastic material opaque to X-radiation arranged around the basic body. At the distal end a balloon member may have been arranged and the marker sleeve may substantially extend over the effective length of the balloon member.

6 Claims, 2 Drawing Sheets

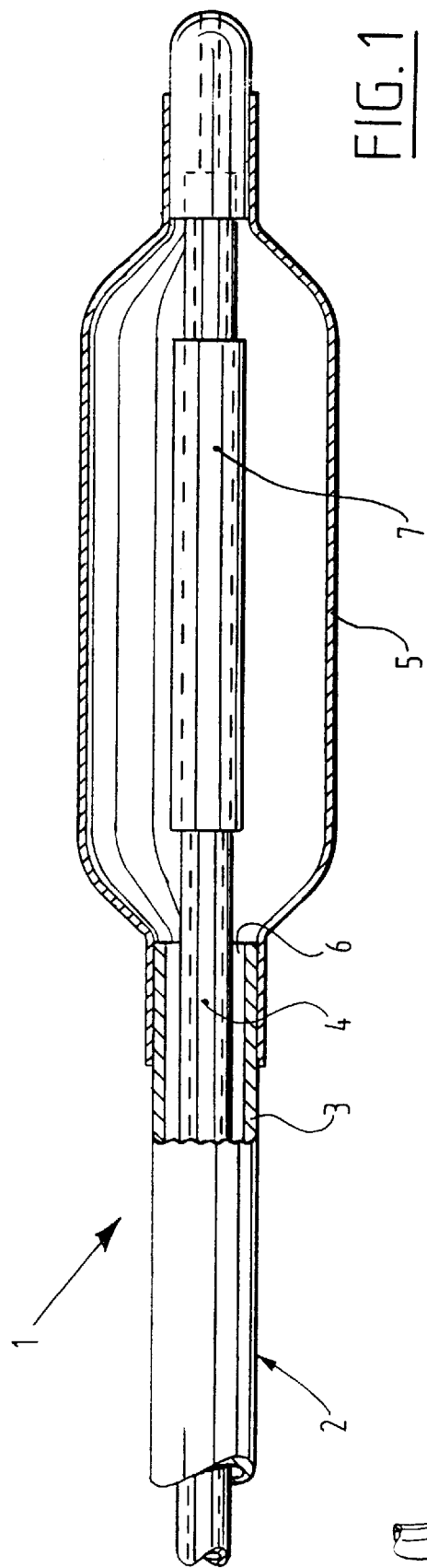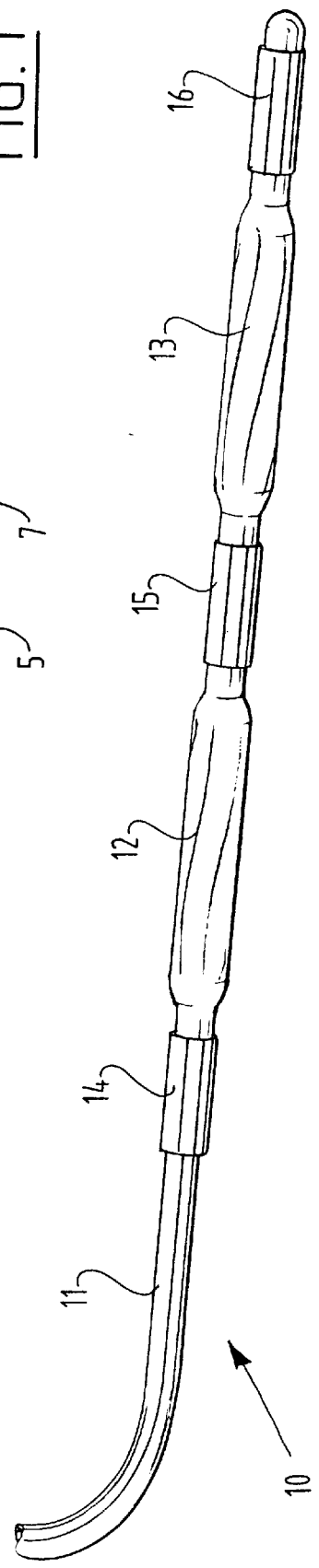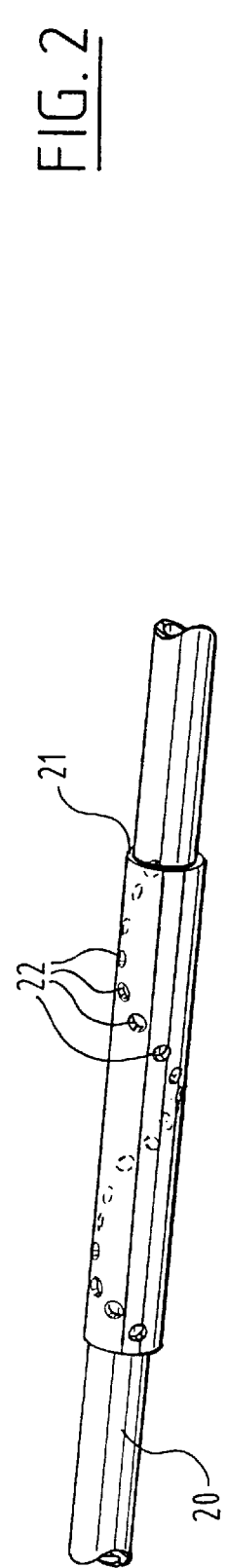

CATHETER WITH MARKER SLEEVE

FIELD OF THE INVENTION

The invention relates to a catheter comprising a tube-like body with a proximal and a distal end. At the distal end, to be inserted into a patient, at least one active element like a balloon member or a sensor has been arranged.

BACKGROUND OF THE INVENTION

It is known to arrange marking rings, made for instance of gold, close to such that active or business end of the catheter. When the catheter is used for the purpose of an investigation or for treatment, the area concerned is visualized by means of X-rays. As the marking rings are opaque to X-radiation, these rings are visible on the X-ray screen, so that the position of the active element can be determined by the physician carrying out the procedure.

These marking rings are difficult to handle and fit when manufacturing the catheter and are addressed by the preset inserter.

SUMMARY OF THE INVENTION

As the radio opaque marker sleeve herein is made of a plastic material, it is pliable and can consequently have a greater length than the known marking rings without affecting the pliability of the catheter in an unfavorable manner. Due to this greater length the market sleeve is more manageable when manufacturing the catheter.

An advantageous further development is characterized herein. Whilst visible on the X-ray screen, the catheter can now be manipulated properly in such a way that the marker sleeve is positioned at the site to be treated. As soon as the sleeve has been positioned carefully at the site to be treated, the balloon member may be expanded, ensuring that exactly the area marked by the marking ring will be treated.

In addition, a more pliable end-section of the catheter or an end-section with a smaller diameter can for instance be marked in this way. And, by arranging a marker sleeve on either side, the active element becomes recognizable on the X-ray screen as an interruption of a continuous line formed by the two marker sleeves positioned in line with one another. Further, because of the holes arranged in the catheter side, an easily recognizable pattern in the image of the marker sleeve on the X-ray screen becomes detectable, so that the marker sleeve cannot be masked so easily by for instance the image of a guide wire or other artifact.

As the distance in between the holes is known, it becomes possible to take measurements from the X-ray screen, whereby the measurements obtained can be related to these distances between the holes.

The marker sleeve may be fixed to the basic body of the catheter by for instance gluing. Preferably the sleeve is however shrunk around the basic body. This may for instance be achieved by first making the marker sleeve swell up in a solvent, as a result of which the sleeve can be pushed easily around the basic body, and by subsequently making this solvent evaporate as a result of which the marker sleeve will resume its original diameter, the size of which will obviously be such, so as to ensure a tight fit of the marker sleeve around the basic body.

The invention will be explained in greater detail with reference to the attached drawings of examples of embodiments.

BRIEF DESCRIPTION OF THE DRAWINGS

FIG. 1 illustrates a distal end-section of a catheter according to the invention, being a balloon catheter;

FIG. 2 shows a partly perspective view of a catheter according to another embodiment of the invention;

FIG. 3 shows a perspective view of a marker sleeve arranged around a catheter in a preferred embodiment.

DETAILED DESCRIPTION OF THE INVENTION

Figure 4:
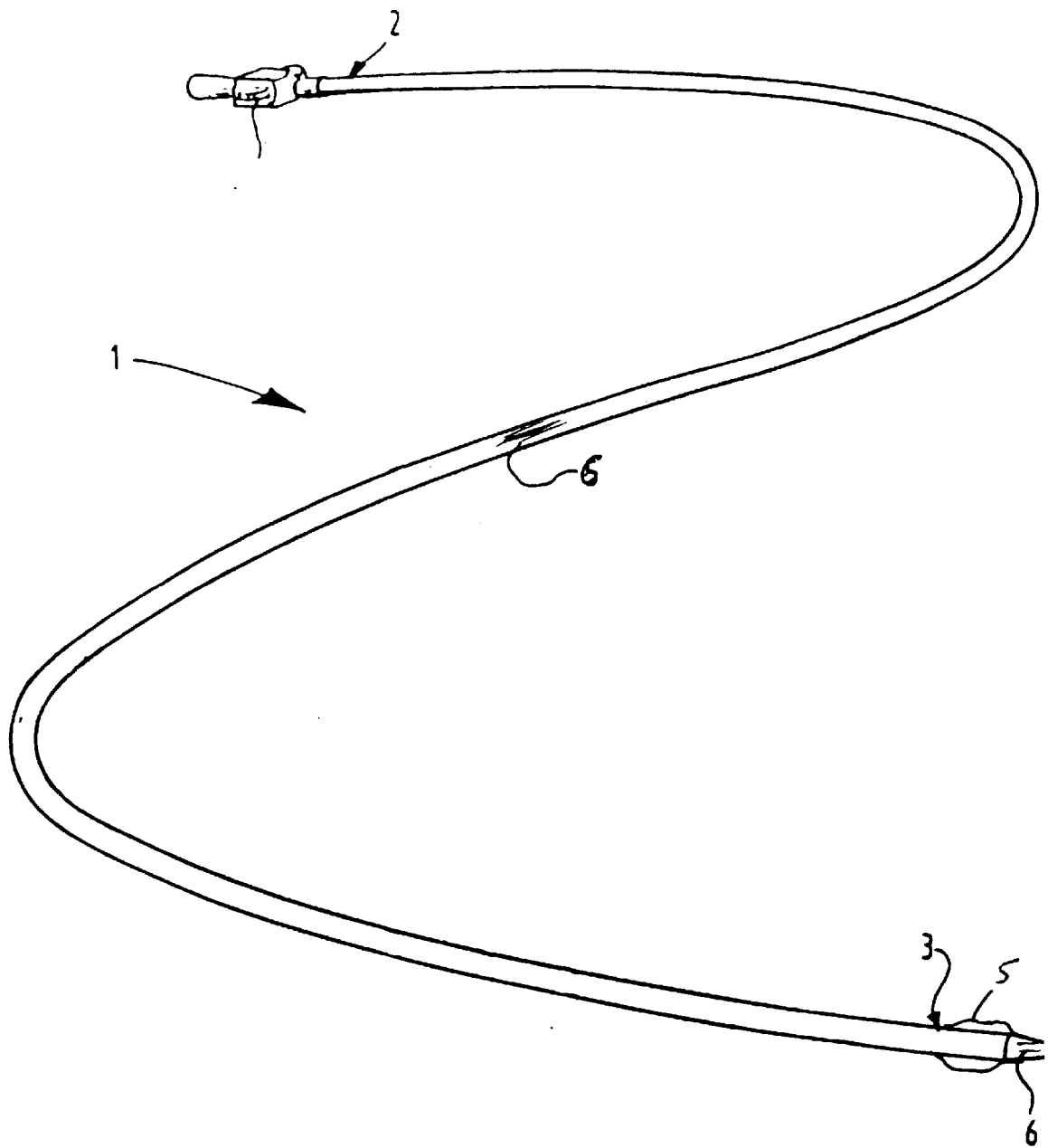
FIG. 4 is a perspective view of the entire catheter of the invention.

The distal end-section of a catheter 1 illustrated in FIG. 1 comprises a balloon member 5 which has been arranged on the tube-like catheter 2 of the catheter 1. Arranged at the proximal end of the catheter are known inflation means, seen for instance in FIG. 4.

The basic catheter body 2 has been made up of an outer tube-like element 3 and an inner tube-like element 4. The inner tube-like element 4 has been received inside a continuous lumen 6 of the outer tube-like element 3. As can be seen in FIG. 1, the inner tube-like element 4 sticks out of the outer tube-like element 3. The balloon member 5 has been arranged around this protruding section. The balloon member 5 can be expanded by supplying a medium under pressure via the lumen 6.

A marker sleeve 7, made of a plastic material opaque to X-radiation, has been arranged around the inner tube-like element 4 at the site of the balloon member 5. This marker sleeve 7 may for instance have been manufactured by means of extrusion of a suitable plastic material. When manufacturing the catheter 1, the marker sleeve 7 is pushed over the inner tube-like element 4 and fixed to it. This may be achieved by means of gluing or for instance by first making the marker sleeve swell up in a solvent, then pushing it over the tube-like element 4 and subsequently evaporating the solvent, as a result of which the marker sleeve 7 will resume the original diameter which fits tightly around the inner tube-like element 4. The marker sleeve has thus been shrunk tightly around the basic body.

As can be seen in FIG. 1 the length of the marker sleeve 7 corresponds to the effective length of the balloon member 5. As it has been made of a plastic material opaque to X-radiation, the position of the marker sleeve 7 will be clearly visible when the end-section of the catheter 1 is made visible on an X-ray screen and it will consequently indicate the position of the active section of the balloon member 5.

As the marker sleeve 7 has been made of a plastic material, it is pliable to such an extend that it does not impede the bending of the basic body of the catheter 1. In addition, the sleeve does not have any sharp edges which could damage the balloon member 5.

The catheter 10 illustrated in FIG. 2 is of a type comprising two balloon members 12, 13 positioned one after the other. The balloon members 12, 13, illustrated here in non-expanded state, are bound by marker sleeves 14, 15, 16 respectively, made of a plastic material opaque to X-radiation. The three marker sleeves 14, 15, 16, which are substantially positioned in line with one another, become clearly visible on the X-ray screen, and the spaces in between the Visible shadows of these marker sleeves consequently indicate the balloons 12 and 13. Thus the physician carrying out the procedure can maneuver the balloons 12 and 13 accurately in the required position.

FIG. 3 shows a marker sleeve 21 arranged around a basic body 20 of a catheter made of a material opaque to X-radiation. This marker sleeve 21 has been provided with holes 22 which are, in the case of this embodiment, positioned on a helical line. The holes 22 have been arranged in a regular fashion, so that they are placed at known distances from one another. The physician carrying out the procedure can take measurements from the X-ray screen, whereby the distances between the holes 22 serve as reference for measurements taken in that area. In addition, the result of the fact that the holes 22 have been arranged to form a pattern is that the image of the marker sleeve becomes very familiar on the X-ray screen, so that also in the case of difficult visual circumstances, for instance due to the presence of other artifacts in the vicinity of the marker sleeve which form a strong shadow on the X-ray screen, it remains easily recognizable. The property of the marker sleeve that it is opaque to X-radiation can be achieved in a manner known as such, for instance by making the marker sleeve of a plastic material which absorbs the X-rays.

As the marker sleeve can be manufactured in such a way that it does not affect the compliance properties of the catheter to a significant degree, it can be made so as to be unusually long for marking means.

We claim:

1. Catheter comprising:

a tube-like body with a proximal and a distal end, marking means arranged close to the distal end made of a material opaque to X-radiation;

whereby the marking means are formed by at least one tube-like marker sleeve made of a plastic material opaque to X-radiation, arranged around the tube-like body;

wherein a balloon marker has been arranged at the catheter distal end and the marker sleeve extends over substantially the entire length of the balloon member; and wherein said tube-like body comprises an outer element and, received inside and partly sticking out of said outer element at its distal end, an inner element, the balloon member extending over the protruding section of said inner element and wherein the marker sleeve has been arranged around the protruding section of the inner element.

2. Catheter as claimed in claim 1, wherein the tube-like body comprises a number of sections with different properties and said marker sleeve has been arranged at the transition points between these sections.

3. Catheter as claimed in claim 1, wherein the catheter comprises at least one element close to its distal end and said marker sleeve has been arranged on either side of this element.

4. Catheter as claimed in claim 1 wherein holes have been arranged in the marker sleeve at predetermined places.

5. Catheter as claimed in claim 4 wherein the holes have been arranged at regular intervals on a helical line.

6. Catheter as claimed in claim 1 wherein the marker sleeve has been shrunk tightly around the tube-like body.

* * * * *